(12) United States Patent
Suzuki et al.

(10) Patent No.: US 10,512,393 B2
(45) Date of Patent: Dec. 24, 2019

(54) VIDEO PROCESSOR

(71) Applicant: OLYMPUS CORPORATION, Tokyo (JP)

(72) Inventors: Tatsuhiko Suzuki, Hino (JP); Yuji Kutsuma, Kokubunji (JP); Hironori Nakagawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 37 days.

(21) Appl. No.: 16/005,819

(22) Filed: Jun. 12, 2018

(65) Prior Publication Data

US 2018/0296077 A1 Oct. 18, 2018

Related U.S. Application Data

(63) Continuation of application No. PCT/JP2016/077321, filed on Sep. 15, 2016.

(30) Foreign Application Priority Data

Dec. 17, 2015 (JP) ................................ 2015-264466

(51) Int. Cl.
*A61B 1/045* (2006.01)
*A61B 1/00* (2006.01)
*H04N 5/232* (2006.01)

(52) U.S. Cl.
CPC .......... *A61B 1/045* (2013.01); *A61B 1/00059* (2013.01); *A61B 1/00174* (2013.01); *A61B 1/00188* (2013.01); *H04N 5/23296* (2013.01)

(58) Field of Classification Search
CPC .. A61B 1/045; A61B 1/00059; A61B 1/00174
(Continued)

(56) References Cited

U.S. PATENT DOCUMENTS

2005/0020879 A1 1/2005 Suzuki
2017/0251911 A1* 9/2017 Ito ...................... G02B 23/2438

FOREIGN PATENT DOCUMENTS

EP 1512365 A1 3/2005
JP H09098945 A 4/1997
(Continued)

OTHER PUBLICATIONS

International Search Report dated Nov. 15, 2016 issued in PCT/JP2016/077321.

*Primary Examiner* — Jeffery A Williams
(74) *Attorney, Agent, or Firm* — Scully, Scott, Murphy & Presser, P.C.

(57) ABSTRACT

A video processor includes an identification section configured to identify a kind of an endoscope, an electronic zoom processing section configured to magnify by a first magnification factor and a second magnification factor larger than the first magnification factor, and a mode setting section configured to set to a first mode of enabling selection of a first processing pattern, and a second processing pattern, when connection of a super-wide angle endoscope is identified, and set to a second mode enabling selection of the second processing pattern when connection of a single visual field endoscope is identified, wherein when the mode setting section performs electronic zoom processing by the second magnification factor in the first mode, the electronic zoom processing section cuts out an image so that only the optical image of the forward visual field is displayed and magnifies the image with the second magnification factor.

3 Claims, 9 Drawing Sheets

(58) Field of Classification Search
USPC .......................................................... 348/76
See application file for complete search history.

(56) References Cited

FOREIGN PATENT DOCUMENTS

| | | | |
|---|---|---|---|
| JP | H09113819 | A | 5/1997 |
| JP | 2004000335 | A | 1/2004 |
| JP | 4856286 | B2 | 1/2012 |
| JP | 4884567 | B2 | 2/2012 |
| WO | 2003101285 | A1 | 12/2003 |
| WO | 2015146836 | A1 | 10/2015 |

* cited by examiner

FIG. 11

| RELEASE 1 | RELEASE 2 | PIP/POP | STRUCTURE/EDGE ENHANCEMENT |
|---|---|---|---|
| COLOR TONE/BRIGHTNESS | OBSERVATION SETTING 1 | OBSERVATION SETTING 2 | SUPER-WIDE ANGLE SCOPE |

BOUNDARY CORRECTION
FORWARD VISUAL FIELD MAGNIFICATION: ON
ELECTRONIC MAGNIFICATION FACTOR
SCALING FACTOR B: 1.2 — 61
SCALING FACTOR C: 1.6 — 62
ELECTRONIC MAGNIFICATION
USE NO SCALING FACTOR B: ON — 63

| RELEASE 1 | RELEASE 2 | PIP/POP | STRUCTURE/EDGE ENHANCEMENT |
|---|---|---|---|
| COLOR TONE/BRIGHTNESS | OBSERVATION SETTING 1 | OBSERVATION SETTING 2 | SUPER-WIDE ANGLE SCOPE |

BOUNDARY CORRECTION
FORWARD VISUAL FIELD MAGNIFICATION: ON
ELECTRONIC MAGNIFICATION FACTOR
SCALING FACTOR B: 1.2 — 61
SCALING FACTOR C: 1.6 — 62
ELECTRONIC MAGNIFICATION
USE NO SCALING FACTOR B: OFF — 63

(60b)

VIDEO PROCESSOR

CROSS REFERENCE TO RELATED APPLICATION

This application is a continuation application of PCT/JP2016/077321 filed on Sep. 15, 2016 and claims benefit of Japanese Application No. 2015-246466 filed in Japan on Dec. 17, 2015, the entire contents of which are incorporated herein by this reference.

BACKGROUND OF THE INVENTION

1. Field of the Invention

The present invention relates to a video processor, and particularly relates to a video processor to which an endoscope that picks up an image of a subject and generates an image signal is connectable.

2. Description of the Related Art

Endoscope systems each including an endoscope that picks up an image of an object inside a subject, an image processing apparatus that generates an observation image of the object the image of which is picked up by the endoscope and the like are widely used in a medical field, an industrial field and the like.

In the endoscope systems as above, endoscope systems each having a super-wide angle endoscope that enables image processing in respective regions of a forward visual field region and a sideward visual field region, and an image processing apparatus to which the super-wide angle endoscope is connectable, have been known in recent years, as shown in the specification of Japanese Patent No. 4856286 and the specification of Japanese Patent No. 4884567.

Electronic zoom processing of cutting out a part of an image in an image pickup signal of an image which is picked up and magnifying or reducing the part of the image has been widely known, and a technique of acquiring an electronic magnified image by cutting out a part of a central portion of an image and performing interpolation and the like is also widely known.

For example, Japanese Patent Application Laid-Open Publication No. 2004-000335 shows an endoscope system including an image processing apparatus that is a video processor (an image processing apparatus) that performs predetermined image processing with an endoscope connected to the video processor, and includes an electronic zoom processing function, and is capable of changing an electronic zoom magnification factor in three steps. Further, Japanese Patent Application Laid-Open Publication No. 9-098945 shows an endoscope system including an image processing apparatus that is a video processor (an image processing apparatus) that performs predetermined image processing with an endoscope connected to the video processor and includes an electronic zoom processing function, and is capable of changing an electronic zoom magnification factor in two steps.

Incidentally, in video processors (image processing apparatuses) each of which can connect to a super-wide angle endoscope as shown in Japanese Patent No. 4856286 or Japanese Patent No. 4884567, and performs predetermined image processing, an example that makes an image of only a forward visual field easier to see by using an electronic zoom processing function as described above when the image of only the forward visual field is shown is known.

More specifically, an example that sets the electronic zoom magnification factor at 1.6 times, for example, to magnify and display the forward visual field region, and displays a subject image with the sideward visual field region omitted, when the subject image is displayed on an observation monitor is known.

As a video processor having the electronic zoom processing function of the kind, a technique of including magnification factors of a plurality of steps (for example, three steps of one time, 1.2 times and 1.6 times) as described above, and being able to set the magnification factor at a magnification factor desired by a user by switching the magnification factors by a toggle operation is also known.

SUMMARY OF THE INVENTION

A video processor of one aspect of the present invention is a video processor provided so that an endoscope that picks up an image of a subject is connectable to the video processor, including an identification section configured to identify a kind of the endoscope which is connected to the video processor, an electronic zoom processing section capable of executing electronic zoom processing of magnifying by a first magnification factor and a second magnification factor larger than the first magnification factor to an image pickup signal of an image picked up by the endoscope, a zoom operation signal input section configured to receive a zoom operation signal from a zoom operation section configured to instruct execution of the electronic zoom processing by the electronic zoom processing section, and a mode setting section configured to set the video processor to a first mode of enabling selection of a first processing pattern that alternately switches a non-execution state of the electronic zoom processing and electronic zoom processing with the second magnification factor each time the zoom operation signal is inputted, and a second processing pattern that cyclically switches the non-execution state of the electronic zoom processing, electronic zoom processing with the first magnification factor and the electronic zoom processing with the second magnification factor each time the zoom operation signal is inputted, when connection of a super-wide angle endoscope that picks up an optical image of a forward visual field and an optical image of a sideward visual field is identified in the identification section, and set the video processor to a second mode enabling selection of the second processing pattern when connection of a single visual field endoscope is identified in the identification section, wherein when the mode setting section performs electronic zoom processing by the second magnification factor in the first mode, the electronic zoom processing section cuts out an image so that only the optical image of the forward visual field is displayed out of the optical image of the forward visual field and the optical image of the sideward visual field and magnifies the image with the second magnification factor.

BRIEF DESCRIPTION OF THE DRAWINGS

FIG. 11 is a view illustrating an example of a menu screen that is generated in a menu screen generation section in the endoscope system including the image processing apparatus of the first embodiment;

FIG. 12 is a view illustrating another example of the menu screen that is generated in the menu screen generation section in the endoscope system including the image processing apparatus of the first embodiment.

DETAILED DESCRIPTION OF THE PREFERRED EMBODIMENTS

Hereinafter, embodiments of the present invention will be described with reference to the drawings.

First Embodiment

A configuration of an endoscope system including an image processing apparatus (a video processor) of a first embodiment will be described with use of FIG. 1 to FIG. 3.

Figure 1:
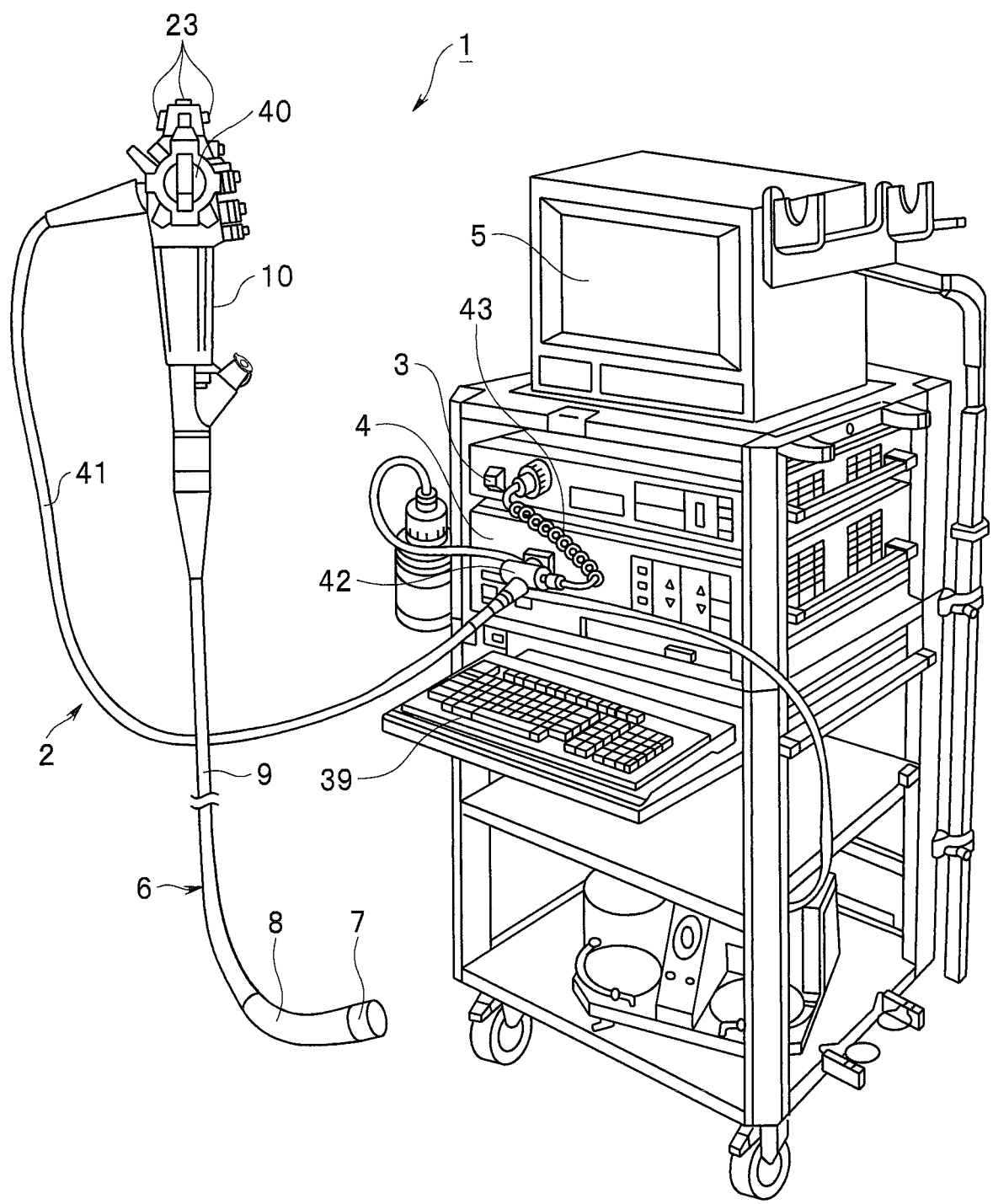
FIG. 1 is a view illustrating a configuration of an endoscope system including an image processing apparatus of a first embodiment of the present invention.
Figure 2:
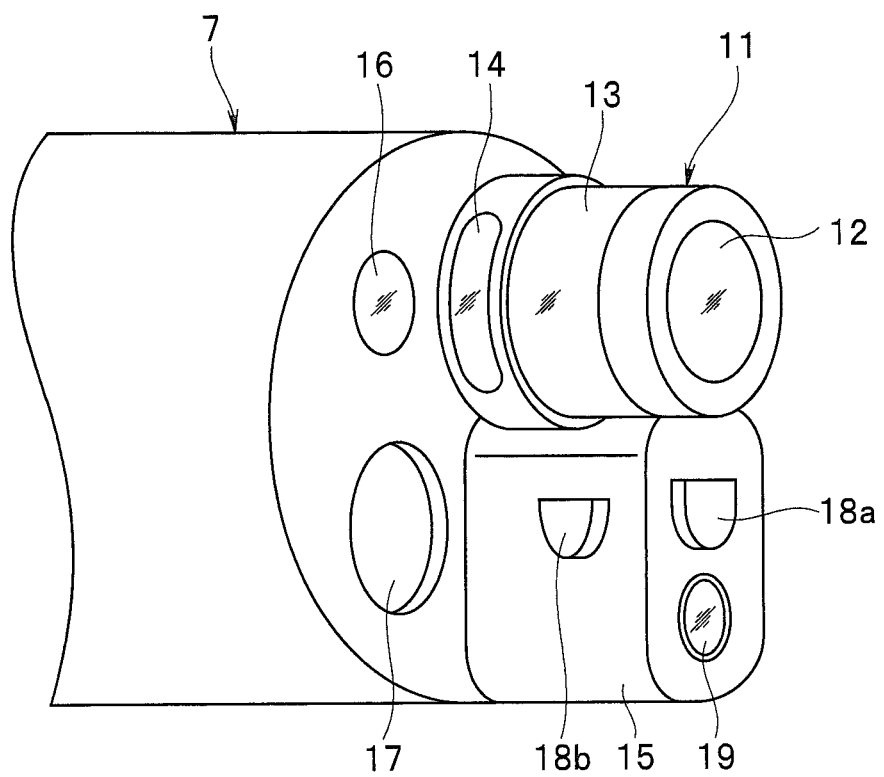
FIG. 2 is a perspective view illustrating a configuration of an insertion portion distal end portion of an endoscope that is connected to the image processing apparatus of the first embodiment.

FIG. 1 is a view illustrating a configuration of the endoscope system including the image processing apparatus of the first embodiment of the present invention, and FIG. 2 is a perspective view illustrating a configuration of an insertion portion distal end portion of an endoscope that is connected to the image processing apparatus of the first embodiment.

Figure 3:
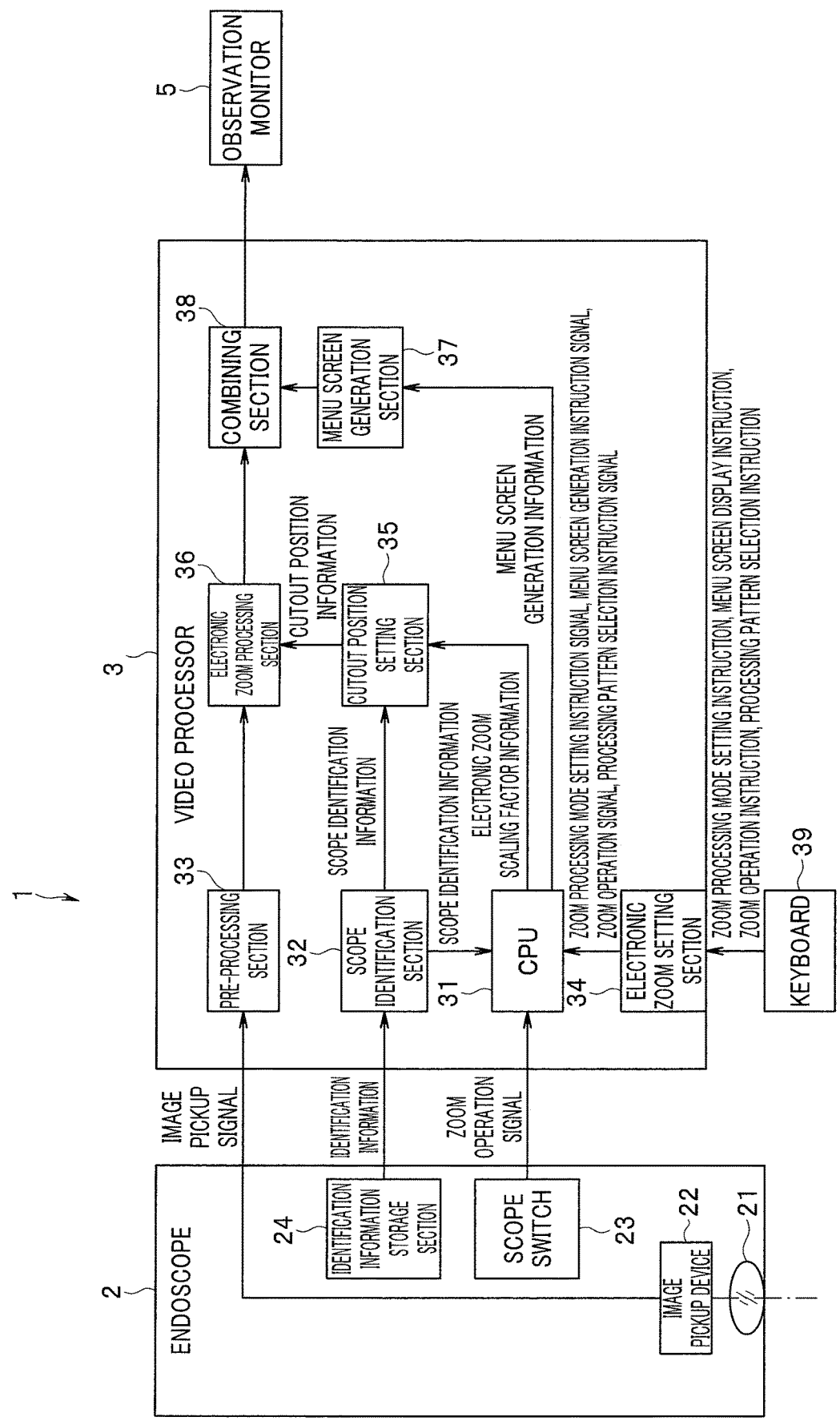
FIG. 3 is a block diagram illustrating an electric configuration of the endoscope system including the image processing apparatus of the first embodiment.

Further, FIG. 3 is a block diagram illustrating an electric configuration of the endoscope system including the image processing apparatus of the first embodiment.

As illustrated in FIG. 1, an endoscope system 1 having the image processing apparatus (hereinafter, a video processor 3) of the first embodiment has a super-wide angle endoscope 2 (hereinafter, an endoscope 2) configured to observe respective regions of a forward visual field region and a sideward visual field region of a subject and be able to pick up images of the respective regions, the video processor 3 configured to be connected to the endoscope 2, receive the image signal and apply predetermined image processing, and have an electronic zoom processing function, a light source apparatus 4 configured to supply illuminating light to illuminate a subject, and a monitor 5 configured to display an observation image corresponding to an image signal.

Note that to the video processor 3, not only the aforementioned super-wide angle endoscope 2 but also an ordinary endoscope by a single visual field is connectable. Further, components of the super-wide angle endoscope 2 that will be shown hereinafter include common components to the single visual field endoscope, but will be explained as components in the super-wide angle endoscope 2 for convenience.

Further, a keyboard 39 for performing various operations including a selection operation of an electronic zoom magnification factor is connected to the video processor 3 (details will be described later).

The endoscope 2 is a super-wide angle endoscope capable of observing a visual field of 180 degrees or more including a forward visual field region and a sideward visual field region as described above, and makes it possible to prevent a lesion in a place that is difficult to see only by observation in a forward direction, such as a back of a fold or a boundary of organs from being overlooked, in a body cavity, in particular, in a large intestine.

Further, the endoscope 2 is configured by having an elongated insertion portion 6 configured to be inserted into a body cavity or the like in a subject, an endoscope operation portion 10 placed at a proximal end side of the insertion portion 6 and configured to be operated by being grasped by a surgeon, and a universal cord 41 having one end portion provided to extend from a side portion of the endoscope operation portion 10.

The insertion portion 6 is configured by having a rigid distal end portion 7 provided at a distal end side, a bendable bending portion 8 provided at a rear end of the distal end portion 7, and a flexible tube portion 9 that is provided at a rear end of the bending portion 8, is long and has flexibility. The bending portion 8 performs a bending action corresponding to an operation of a bending operation lever 40 provided at the endoscope operation portion 10.

In a distal end portion 7 in the insertion portion 6 of the endoscope 2 according to the present embodiment, an objective optical system 21 (refer to FIG. 3) having a first objective optical system that forms an optical image of a forward visual field, and a second objective optical system that forms an optical image of a sideward visual field that is a visual field around the forward visual field, and an image pickup device 22 (refer to FIG. 3) configured to pick up optical images formed in the first and second objective optical systems in the objective optical system 21 are placed. Note that a detailed configuration of the distal end portion 7 such as the objective optical system 21 will be described later.

The image pickup device 22 is an image pickup section that is disposed so that a visual field center F (refer to FIG.

Figure 5:
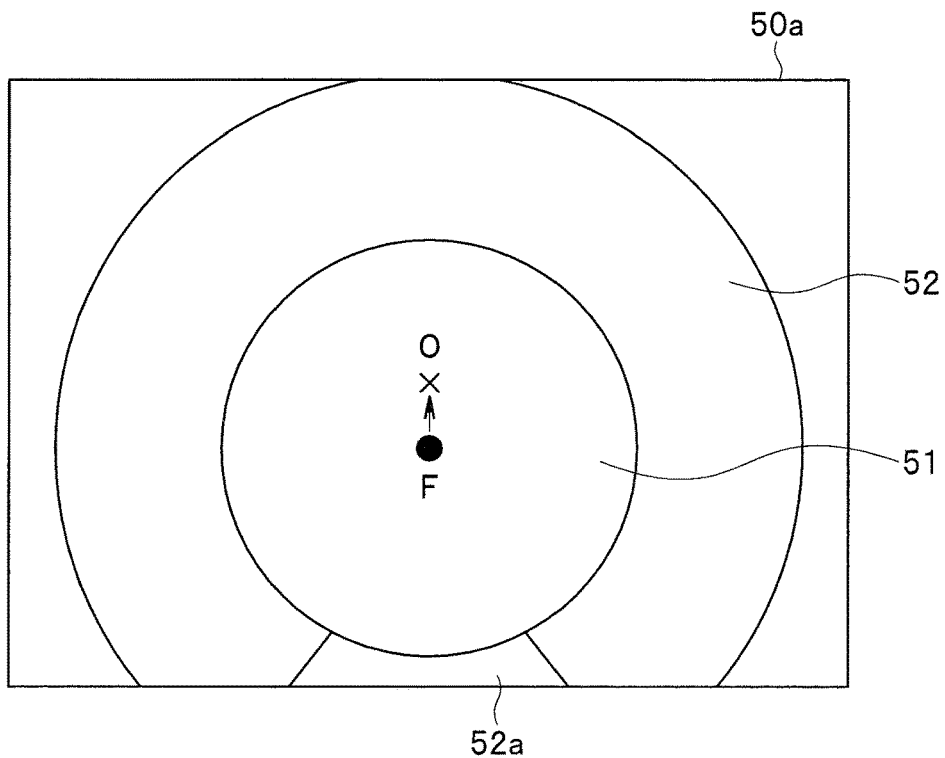
FIG. 5 is a view illustrating an example of a screen at a time of an image expressed by an image pickup signal outputted from an image pickup device being displayed on an observation monitor, in the endoscope system including the image processing apparatus of the first embodiment.

5 and the like) of the objective optical system 21 deviates from a center of an image pickup range (corresponding to a center O of a cutout region in a case of a zoom scaling factor of one time illustrated in FIG. 5), and is configured to pick up an optical image of an object formed by the objective optical system 21 to generate an image pickup signal.

Further, a scope switch 23 for executing various operation instructions is placed at the endoscope operation portion 10 of the endoscope 2, and is connected to a CPU 31 (refer to FIG. 3) in the video processor 3 via the universal cord 41.

The scope switch 23 is a switch for performing various operations relating to the endoscope 2, and has functions of, a freeze switch for picking up a still image, an air feeding/water feeding switch, a zoom switch for performing electronic zoom operation and the like, but in the present embodiment, the scope switch 23 performs a function as a zoom operation section that instructs execution of electronic zoom processing.

A connector 42 is provided at a proximal end side of the universal cord 41, and the connector 42 is connected to the light source apparatus 4. That is, a pipe sleeve (not illustrated) which is a connection end portion of a fluid conduit that protrudes from a distal end of the connector 42, and a light guide pipe sleeve (not illustrated) which is a supply end portion of illuminating light are detachably connected to the light source apparatus 4.

Further, one end of a connection cable 43 is connected to an electric contact portion provided on a side surface of the connector 42. In the connection cable 43, a signal line that transmits an image pickup signal from the image pickup device 22 (refer to FIG. 3) in the endoscope 2, for example, is internally provided, and a connector portion at the other end is connected to the video processor 3.

Note that in the connector 42, an identification information storage section 24 (refer to FIG. 3) storing peculiar predetermined ID information in the endoscope 2 is placed.

The identification information storage section 24 is a storage section that stores peculiar identification information in the endoscope 2 in a nonvolatile manner, and a model number and a serial number of the endoscope 2, a size and a number of pixels of the image pickup device 22, disposition information indicating a position in design of the visual field center F of the objective optical system 11 to the center of the image pickup range of the image pickup device 22 and the like are stored in advance at the time of manufacture.

Next, with reference to FIG. 2, a configuration of the distal end portion 7 in the insertion portion 6 of the endoscope 2 will be described.

In the distal end portion 7 of the insertion portion 6, a cylindrical portion 11 that protrudes in an insertion axis direction from a distal end surface is provided. In the cylindrical portion 11, the aforementioned objective optical system 21 is placed as an optical system having a first objective optical system that forms an optical image of a forward visual field, and a second objective optical system that forms an optical image of a sideward visual field that is a visual field around the forward visual field.

That is, the objective optical system 21 is configured to acquire a forward visual image by an object light of a forward visual field that is a visual field in a direction of the visual field center F (accordingly, the visual field center F is a center of the forward visual field) via a forward observation window 12 placed on a distal end surface of the cylindrical portion 11, and acquire a sideward visual field image by an object light from a sideward visual field that is a visual filed sideward in a direction of the visual field center F via a sideward observation window 13 that is placed on a circumferential surface of the cylindrical portion 11.

In this way, the endoscope 2 according to the present embodiment is configured as a super-wide endoscope that acquires a forward visual field image and a sideward visual field image.

Further, at a proximal end portion of the cylindrical portion 11, a sideward illuminating window 14 that emits illuminating light to a sideward visual field range from the sideward observation window 13 is provided, and on the distal end surface of the distal end portion 7, a forward illumination window 16 that emits an illuminating light to a forward visual field range from the forward observation window 12 is provided.

Further, on the distal end surface of the distal end portion 7, a channel opening portion 17 of a treatment instrument channel is provided, and a support portion 15 that protrudes in an insertion axis direction along a part of the circumferential surface of the aforementioned cylindrical portion 11 (adjacently to a circumferential surface at a lower side of the cylindrical portion 11 in FIG. 2) is provided.

On a distal end surface of the support portion 15, a forward illumination window 19 that emits an illuminating light to the forward visual field range from the forward observation window 12, and a forward observation window nozzle portion 18*a* for injecting a fluid that cleans the forward illumination window 19 are provided. Further, on a side surface of the support portion 15, a sideward observation window nozzle portion 18*b* for injecting a fluid that cleans the sideward observation window 13 is provided.

The endoscope 2 configured like this includes the support portion 15 that is a structure provided at a position that blocks a part of an object light from an object from being incident on the objective optical system 21, that is, here, the support portion 15 covers a part of the circumferential surface of the cylindrical portion 11, and blocks a part of the object light that is incident from the sideward visual field by the sideward observation window 13, so that it is unavoidable that optical vignetting occurs to a part of the optical image which is formed (here, a part of the sideward visual field, for example).

FIG. 5 is a view illustrating an example of a screen 50*a* at a time of an image expressed by an image pickup signal outputted from the image pickup device being displayed on an observation monitor 5, in the endoscope system including the image processing apparatus of the first embodiment.

As illustrated in the drawings, a forward visual field image 51 that is formed by an object light from the forward observation window 12 forms a circle with the visual field center F as a center. Further, a sideward visual field image 52 formed by an object light from the sideward observation window 13 is formed into a substantially annular shape in an outer circumferential portion of the forward visual field image 51. Here, the reason why the annular shape of the sideward visual field image 52 is described as substantial is that a part of a circumferential direction of the sideward visual field image 52 becomes vignetting 52*a* by the aforementioned support portion 15.

Therefore, the image pickup device 22 is disposed in such a manner that the center of the image pickup range is displaced to an opposite direction from the vignetting 52*a* from the visual field center F of the objective optical system 21 such that the vignetting 52*a* of the optical image of an object formed in the image pickup range by the support portion 15 that is a structure becomes small.

<Configuration of Video Processor 3>

Next, an electric configuration of a video processor 3 that is an image processing apparatus of the first embodiment and the endoscope system 1 including the video processor 3 will be described.

FIG. 3 is a block diagram illustrating the electric configuration of the endoscope system including the image processing apparatus of the first embodiment.

As illustrated in FIG. 3, the video processor 3 of the first embodiment includes the CPU 31 for controlling respective circuits in the video processor 3 and respective circuits in the endoscope 2 which is connected, a pre-processing section 33, a scope identification section 32, an electronic zoom setting section 34, a cutout position setting section 35, an electronic zoom processing section 36, a menu screen generation section 37 and a combining section 38.

Further, as described above, to the video processor 3, a keyboard 39 for performing various operations including a selection operation of an electronic zoom magnification factor such as setting of a zoom processing pattern is connected.

The pre-processing section 33 performs various kinds of pre-processing such as predetermined gain adjustment and A/D conversion to the image pickup signal outputted from the image pickup device 22.

The scope identification section 32 is configured to identify a type of the endoscope which is connected to the video processor 3 based on identification information outputted from the identification information storage section 24, and output information (scope identification information) relating to the identification result to the CPU 31.

More specifically, the scope identification section 32 identifies whether or not the endoscope is an endoscope in which the center of the image pickup range of the endoscope which is connected to the video processor 3 at present and the visual field center F of the objective optical system 21 correspond to each other based on the model number information or the like, in the identification information that is stored in the identification information storage section 24.

Here, an endoscope in which the center of the image pickup range and the visual field center F of the objective optical system 21 do not correspond to each other is the super-wide angle endoscope 2 having the forward visual field and the sideward visual field filed as illustrated in FIG. 2, for example, and the endoscope in which the center of the image pickup range and the visual field center F of the objective optical system 21 correspond to each other is an ordinary endoscope of a single visual field, for example.

Note that in the present embodiment, the scope identification section 32 performs a function as an identification section that identifies a kind of the endoscope which is connected.

The electronic zoom setting section 34 is capable of connecting to the keyboard 39, and receives a predetermined operation instruction signal from the keyboard 39 under control of the CPU 31.

That is, various operation instruction signals including a zoom processing mode setting instruction, a menu screen display instruction, a processing pattern selection instruction and a zoom operation instruction can be inputted to the electronic zoom setting section 34 by a keyboard 39 operation by a user.

The electronic zoom setting section 34 is configured to transmit a zoom processing setting signal, a menu screen generation instruction signal, a processing pattern selection instruction signal or a zoom operation signal to the CPU 31 in accordance with the instructions.

More specifically, the electronic zoom setting section 34 is configured to generate a "zoom processing mode setting instruction signal", and transmit the zoom processing mode setting instruction signal to the CPU 31, when the electronic zoom setting section 34 receives the zoom processing mode setting instruction from the keyboard 39. The "zoom processing mode setting instruction signal" is an instruction signal for selectively setting either a first processing mode (a super-wide angle endoscope zoom processing mode) or a second processing mode (a zoom processing mode for a single visual field endoscope) that will be described later.

The CPU 31 that receives the "zoom processing mode setting instruction signal" is configured to perform predetermined control of transmitting predetermined information to the menu screen generation section 37 and the like in accordance with the kind of the instructed zoom processing mode (the zoom processing mode will be described in detail later).

Further, the electronic zoom setting section 34 is configured to be instructed to set the first processing mode as the zoom processing mode by the operation of the keyboard 39 by the user described above, generate a "menu screen generation instruction signal" when the electronic zoom setting section 34 receives a menu screen display instruction, and transmit the menu screen generation instruction signal to the CPU 31. The "menu screen generation instruction signal" is an operation instruction signal for displaying a menu screen exclusive to a super-wide angle endoscope on the monitor 5.

Subsequently, the CPU 31 which receives the "menu screen generation instruction signal" is configured to transmit predetermined "menu screen generation information" to the menu screen generation section 37 (details will be described later).

Further, the electronic zoom setting section 34 is configured to generate a "processing pattern selection instruction signal" and transmit the processing pattern selection instruction signal to the CPU 31, when the electronic zoom setting section 34 receives a processing pattern selection instruction from the keyboard 39 by the operation of the user. The "processing pattern selection instruction signal" is an instruction signal for selectively switching one processing pattern of the plurality of kinds of processing patterns (the processing patterns relating to change of a number of changing steps of the electronic zoom magnification factor).

Further, the electronic zoom setting section 34 is configured to generate a "zoom operation signal" and transmits the zoom operation signal to the CPU 31, when the electronic zoom setting section 34 receives a zoom operation instruction from the keyboard 39 by the operation of the user. The "zoom operation signal" is an operation instruction signal similar to the "zoom operation signal" that is transmitted from the zoom switch 23 in the aforementioned endoscope 2.

That is, the electronic zoom setting section 34 and the keyboard 39 are configured to perform a function as a zoom operation section that instructs execution of the electronic zoom processing under control of the CPU 31 similarly to the zoom switch 23 in the aforementioned endoscope 2, and output the "zoom operation signal" which is an operation signal for setting the scaling factor of the zoom magnification factor to the CPU 31.

Note that as described above, the zoom operation signal which is generated in the electronic zoom setting section 34 or the scope switch 23 is inputted to the CPU 31, and the CPU 31 performs a function as a zoom operation signal input section to which the zoom operation signal is inputted.

Further, the CPU 31 is configured to generate electronic zoom scaling factor information corresponding to the number of steps in the processing pattern based on the processing pattern information which will be described later each time the CPU 31 receives the zoom operation signal when the CPU 31 receives the zoom operation signal, and output the electronic zoom scaling factor information to the cutout position setting section 35 (the zoom operation signal and the processing pattern will be described in detail later).

Note that as described above, in the present embodiment, the keyboard 39 outputs various operation instruction signals including the zoom processing mode setting instruction, the menu screen display instruction, the zoom operation instruction and the processing pattern selection instruction by the operation of the user, and the electronic zoom setting section 34 transmits the zoom processing mode setting instruction signal, the menu screen generation instruction signal, the zoom operation signal or the processing pattern selection instruction signal in accordance with the instructions, but the respective instructions may be performed by the electronic zoom setting section 34 itself.

For example, the electronic zoom setting section 34 may be configured as an operation panel placed in the video processor 3, and may be made to output various operation instruction signals including the zoom processing mode setting instruction, the menu screen display instruction, the zoom operation instruction and the processing pattern selection instruction by the operation of the operation panel.

Further, in place of the keyboard 39 which is connected to the electronic zoom setting section 34, for example, operation means such as a foot switch not illustrated is connected, and the foot switch or the like may perform a function as the aforementioned zoom operation section.

The cutout position setting section 35 is configured to set a cutout region that is a part of the picked up image that is an image expressed by an image pickup signal based on the electronic zoom scaling factor information acquired from the CPU 31 under control of the CPU 31.

Further, the cutout position setting section 35 receives scope identification information from the scope identification section 32 under control of the CPU 31, and performs correction of a cutout region which is set by using disposition information indicating a position in design of the visual field center F of the objective optical system 21 to the center of the image pickup range of the image pickup device 22 which is acquired from the scope identification section 32 when the connected endoscope is determined as the super-wide angle endoscope 2, for example.

Subsequently, the cutout position setting section 35 is configured to set a position and a size of the cutout region so that the center O of the cutout region is closer to the visual field center F as the zoom scaling factor increases to 1.2 times, 1.4 times, . . . , for example, from one time (that is, a non-executing state of the electronic zoom processing) as described later (note that the cutout position setting section 35 may further instruct the position and the size of the cutout region based on positional information of the support portion 15).

Further, the cutout position setting section 35 outputs information concerning the position and the size of the cutout region which are set to the electronic zoom processing section 36 as cutout position information.

The electronic zoom processing section 36 cuts out the cutout region which is set by the cutout position setting section 35 from the endoscope image signal which is processed by the pre-processing section 33, performs magnification or reduction in accordance with an electronic zoom scaling factor, and generates a zoom image.

Figure 4:
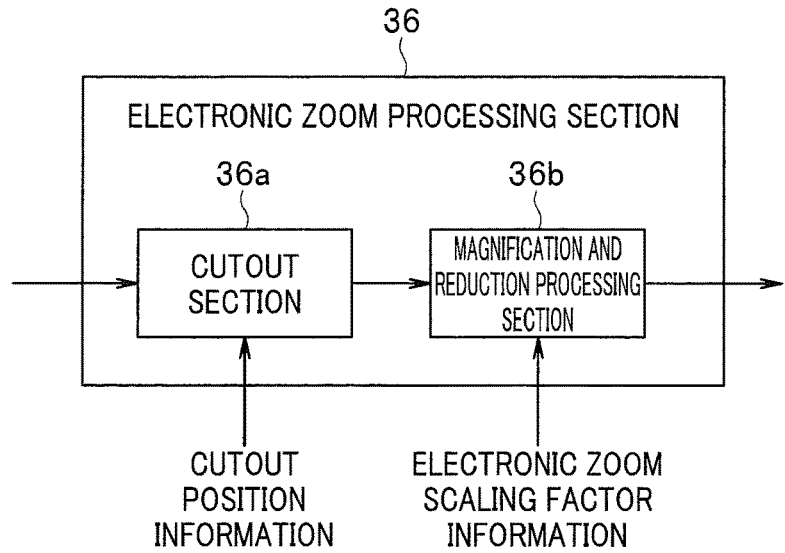
FIG. 4 is a block diagram illustrating a configuration of an electronic zoom processing section in the image processing apparatus of the first embodiment.

Here, a configuration of the electronic zoom processing section 36 will be described with reference to FIG. 4. FIG. 4 is a block diagram illustrating a configuration of the electronic zoom processing section in the image processing apparatus of the first embodiment.

As illustrated in FIG. 4, the electronic zoom processing section 36 includes a cutout section 36a and a magnification and reduction section 36b.

The cutout section 36a cuts out the cutout region from the image which is inputted from the pre-processing section 33 based on the cutout position information (when the cutout region is a rectangular region, the cutout position information is configured by including positional information of an upper left corner and positional information of a lower right corner of the cutout region, or configured by including the positional information of the upper left corner and a number of pixels in a horizontal direction and a number of pixels in a vertical direction of the cutout region, or the like).

The magnification and reduction section 36b performs pixel interpolation or the like so that a pixel configuration (the number of pixels in the vertical direction and the number of pixels in a lateral direction) of the image data of the cutout region which is cut out from the cutout section 36a corresponds to a pixel configuration of the image data which is displayed on the observation monitor 5, based on the electronic zoom scaling factor information acquired via the cutout position setting section 35.

Here, the electronic zoom processing section 36 performs a function as an electronic zoom processing section that can execute electronic zoom processing of magnifying an image relating to the image signal by a plurality of magnification factors including at least a first magnification factor (for example, 1.2 times) and a second magnification factor (for example, 1.6 times) that is larger than the first magnification factor, to the endoscope image signal.

The menu screen generation section 37 has a function of generating a menu screen signal exclusive to a super-wide angle endoscope under control of the CPU 31.

That is, the menu screen generation section 37 is configured to receive the "menu screen generation information" from the CPU 31 in accordance with an operation of the keyboard 39 or the like, and generate the menu screen exclusive to a super-wide angle endoscope.

More specifically, the menu screen generation section 37 receives the menu screen generation information from the CPU 31, generates a menu screen signal exclusive to a super-wide angle endoscope as illustrated in FIG. 11 and FIG. 12, for example, and transmits the menu screen signal exclusive to a super-wide angle endoscope to the combining section 38 (note that the menu screen exclusive to a super-wide angle endoscope will be described in detail later).

The combining section 38 combines the endoscope image signal which goes through the processing in the electronic zoom processing section 36 and the menu screen signal generated in the menu screen generation section 37 or switches the signals to output the combined signal or the switched signal to the observation monitor 5.

<Specific Example of Endoscope Image Display by Change in Electronic Zoom Magnification Factor>

Next, a specific example of an endoscope image by a step change of the zoom magnification factor by the electronic zoom processing in the present embodiment will be described.

Figure 6:
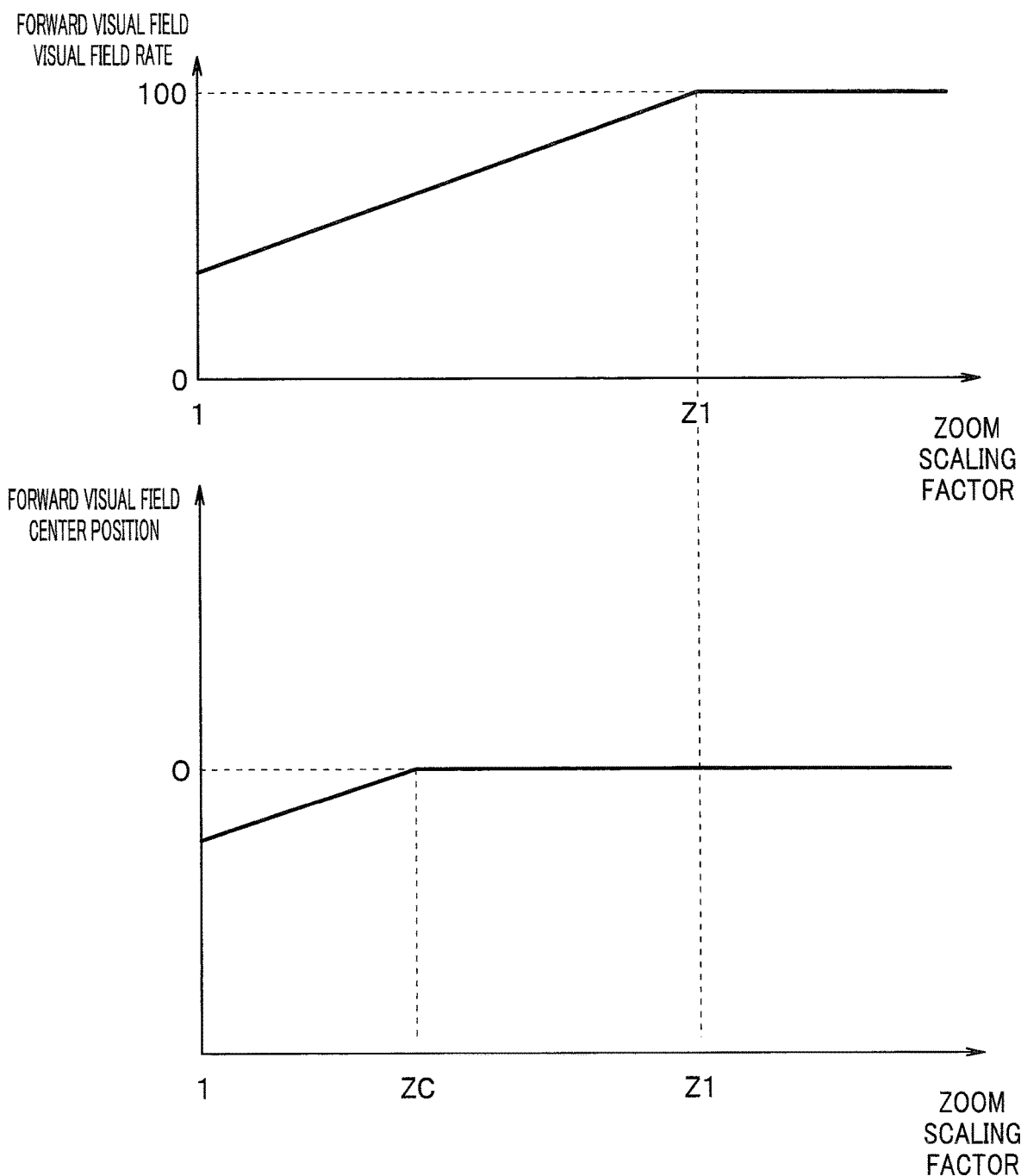
FIG. 6 is a diagram illustrating a state in which a visual field center approaches a center of a cutout region, and a visual field ratio of a forward visual field comes close to 100%, in accordance with a change in zoom scaling factor, in the endoscope system including the image processing apparatus of the first embodiment.

FIG. 6 is a diagram illustrating a state in which the visual field center approaches the center of the cutout region, and the visual field ratio of the forward visual field is close to 100% in accordance with the change in the zoom scaling factor in the endoscope system including the image processing apparatus of the first embodiment, and FIG. 7 to FIG. 10 are views illustrating display examples of a screen 50a of the observation monitor 5 at times of the zoom scaling factors being respectively one time (FIG. 7), 1.2 times (FIG. 8), 1.4 times (FIG. 9) and 1.6 times (FIG. 10) in the endoscope system including the image processing apparatus of the first embodiment.

Figure 7:
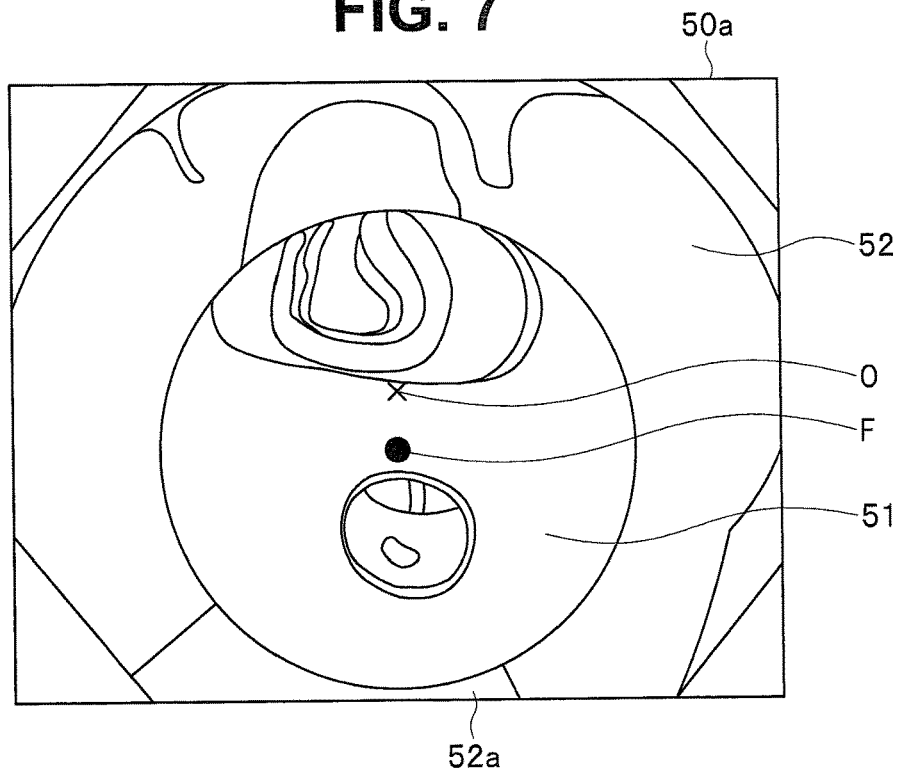
FIG. 7 is a view illustrating one display example of the screen of the observation monitor at a time of the zoom scaling factor being one time in the endoscope system including the image processing apparatus of the first embodiment.

When zoom processing is non-execution state, that is, zoom magnification is not performed, and a zoom scaling factor is one time in the electronic zoom processing section 36 in the present embodiment, the visual field center F which is the center position of the forward visual field is located, for example, in a position which is displaced downward of the center O of the cutout region (corresponding to the center of the image pickup range at the time of one time), and the visual field ratio which is a ratio of the forward visual field image to the endoscope image display region of the screen 50a also remains around at 50% or less, for example, as illustrated in FIG. 5 and FIG. 7.

Figure 8:
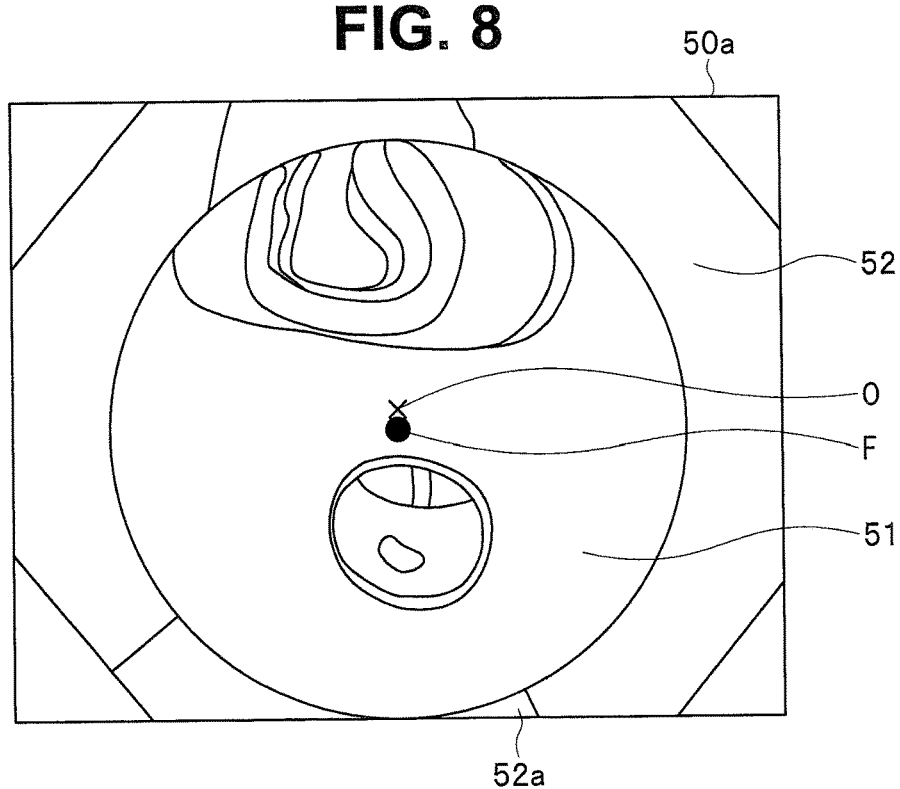
FIG. 8 is a view illustrating one display example of the screen of the observation monitor at a time of the zoom scaling factor being 1.2 times in the endoscope system including the image processing apparatus of the first embodiment.

When the zoom scaling factor increases from the one time in the electronic zoom processing section 36, zoom magnification is performed so that the visual field center F approaches the center O of the cutout region as seen from an observer side of the observation monitor 5 (as processing on a video processor 30 side, the cutout region is set so that the center O of the cutout region approaches the visual field center F) as shown by an arrow in FIG. 5, and the visual field ratio of the forward visual field also increases with increase in the zoom scaling factor (refer also to FIG. 8 in combination).

Figure 9:
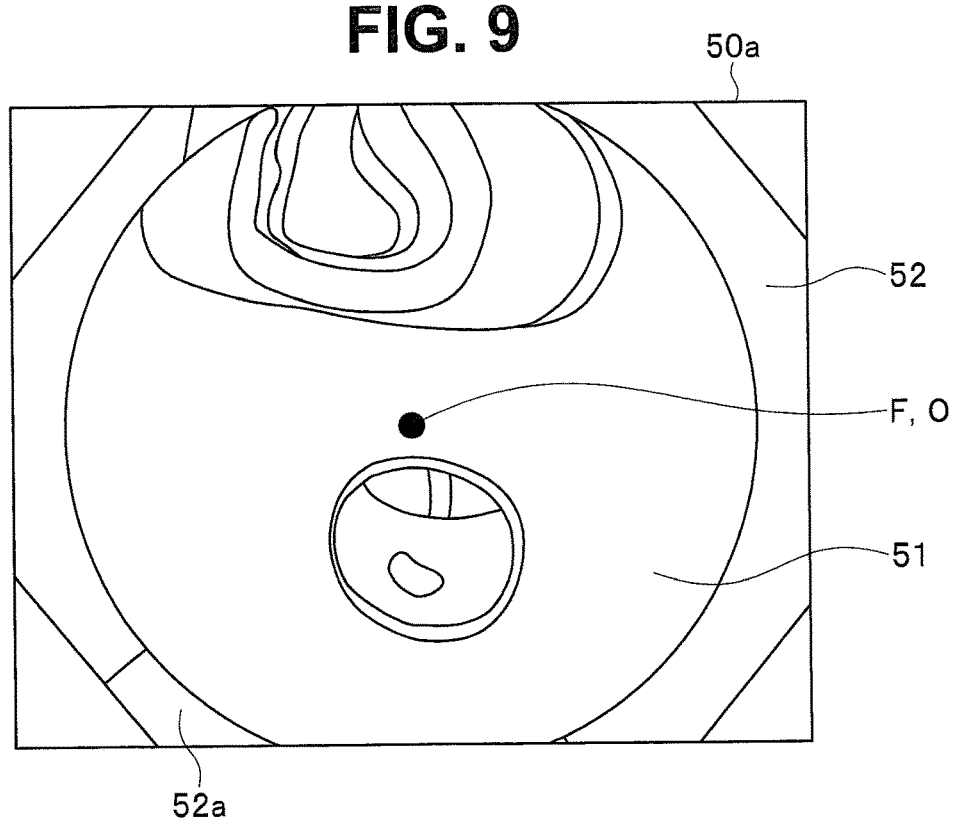
FIG. 9 is a view illustrating one display example of the screen of the observation monitor at a time of the zoom scaling factor being 1.4 times in the endoscope system including the image processing apparatus of the first embodiment.

When the zoom scaling factor becomes ZC illustrated in FIG. 6 in the electronic zoom processing section 36, the visual field center F corresponds to the center O of the cutout region, and screen display as illustrated in FIG. 9 is performed, for example. In the zoom region where a subsequent zoom scaling factor is ZC or more, the visual field center F remains to correspond to the center O of the cutout region.

Figure 10:
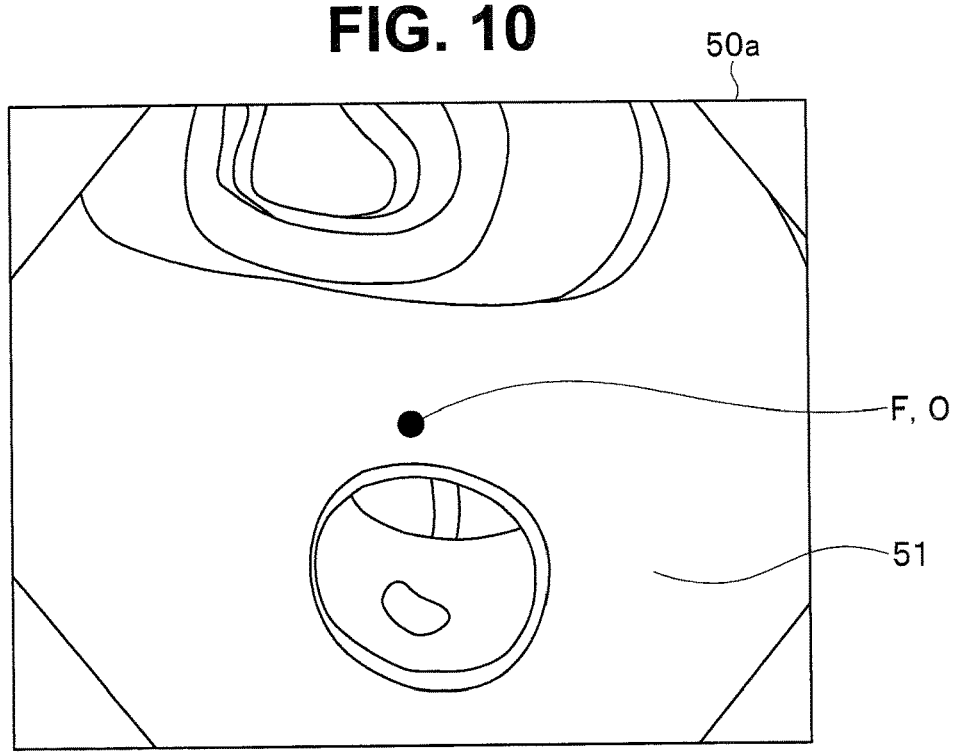
FIG. 10 is a view illustrating one display example of the screen of the observation monitor at a time of the zoom scaling factor being 1.6 times in the endoscope system including the image processing apparatus of the first embodiment.

Further, when the zoom scaling factor becomes Z1 in FIG. 6 in the electronic zoom processing section 36, the visual field ratio of the forward visual field reaches 100%. In the zoom region where the subsequent zoom scaling factor is Z1 or more, the visual field ratio of the forward visual field remains to be 100%. Accordingly, in the endoscope image display region of the screen 50a, only the forward visual field image is displayed as illustrated in FIG. 10, for example.

Note that Z1>ZC is satisfied in the example illustrated in FIG. 6, and this is because the forward visual field image 51 formed by an object light forms a circular shape, for example, whereas the endoscope image display region of the screen 50a forms an octagon, for example, so that the vignetting 52a moves outside the visual field of the endoscope image display region before the visual field ratio of the forward visual field reaches 100%, and when the vignetting 52a is out of the visual field, it is not necessary for the visual field center F to deviate from the center O of the cutout region, but rather it is better to match the visual field center F and the center O, even if the visual field ratio is less than 100%.

However, when the endoscope image display region forms a circular shape, for example, Z1=ZC may be established. When the visual field ratio of the forward visual field reaches 100%, the vignetting 52a is not inside the visual field of the endoscope image display region, so that it is not inevitable that the visual field center F deviates from the center O of the cutout region, and it is not necessary that Z1<ZC is satisfied.

In this way, according to the present embodiment, the zoom image is generated by setting the cutout region so that as the zoom scaling factor increases, the center O of the cutout region approaches the visual field center F, and therefore an electronic zoom image which is easy to see can be obtained from the image pickup signal in which the visual field center F deviates from the center of the image pickup range.

That is, when the zoom scaling factor is low, it is possible to prevent the vignetting 52a from being displayed as much as possible, and when the zoom scaling factor is high, the vignetting 52a is not displayed at all and the visual field center F approaches and corresponds to the center O of the cutout region (that is, the center of the screen 50a which is displayed), so that electronic zoom can be performed while a balance of display is kept.

Subsequently, when the visual field ratio of the forward visual field reaches 100%, observation can be performed in a similar visual field to the visual field of the ordinary endoscope with a single visual field.

Next, a zoom processing pattern and a zoom processing mode according to the electronic zoom processing in the present embodiment will be described.

<Types of Zoom Processing Pattern>

As described above, the video processor 3 of the present embodiment enables electronic zoom processing by a plurality of kinds of magnification factors.

More specifically, electronic zoom processing by zoom magnification factors (zoom scaling factors) of, for example, one time (a non-execution state of electronic zoom processing), 1.2 times, 1.4 times and 1.6 times is enabled, a magnification factor corresponding to an arbitrary number of multiple steps is selected from these plurality of kinds of magnification factors, and zoom processing can be performed by switching the magnification factors cyclically in accordance with a predetermined operation.

Further, the video processor 3 of the present embodiment has two processing patterns concerning the zoom processing.

More specifically, the present embodiment has two processing patterns of a first processing pattern: a processing pattern with two steps capable of alternately switching a non-execution state (including one time) of the electronic zoom processing, and electronic zoom processing with a second magnification factor (for example, 1.6 times), and a second processing pattern: a processing pattern with three steps in which the non-execution state (including one time) of the electronic zoom processing, electronic zoom processing with a first magnification factor (1.2 times, for example), and the electronic zoom processing with the second magnification factor (1.6 times, for example) are cyclically switched.

Further, in both of the aforementioned first processing pattern and second processing pattern, each of the magnification factors is switched in accordance with the number of steps each time the scope switch 23 or the keyboard 39 (the electronic zoom setting section 34) is operated, in other words, each time a "zoom operation signal" is inputted to the CPU from the scope switch 23 or the electronic zoom setting section 34.

More specifically, in the first processing pattern, each time the scope switch 23 or the keyboard 39 (the electronic zoom setting section 34) is operated, the cutout position setting section 35 and the electronic zoom processing section 36 act under control of the CPU 31, the non-execution state (including one time) of the electronic zoom processing and the electronic zoom processing with the second magnification factor (1.6 times, for example) are alternately switched (switching processing in two steps).

Further, in the second processing pattern, each time the scope switch 23 or the keyboard 39 (the electronic zoom setting section 34) is operated, the cutout position setting section 35 and the electronic zoom processing section 36 act under control of the CPU 31 as described above, the non-execution state (including one time) of the electronic zoom processing, the electronic zoom processing with the first magnification factor (1.2 times, for example), and the electronic zoom processing with the second magnification factor (1.6 times, for example) are cyclically switched (the cyclic switching processing in three steps).

Note that in the present embodiment, the aforementioned two processing patterns are adopted, but a processing pattern in four steps, or processing patterns in which the respective zoom scaling factors are changed may be adopted regardless of the two processing patterns.

<Setting of Zoom Processing Mode>

The CPU 31 and the electronic zoom setting section 34 in the video processor 3 in the present embodiment selectively set the zoom processing mode as shown below by receiving the zoom processing mode setting instruction from the keyboard 39.

Here, more specifically, the present embodiment has two zoom processing modes of A first processing mode: a zoom processing mode for a super-wide angle endoscope in the case of the endoscope connected to the video processor 3 being the super-wide angle endoscope 2, and A second processing mode: a zoom processing mode for a single visual field endoscope in the case of the endoscope connected to the video processor 3 being an endoscope of a single visual field other than the super-wide angle endoscope 2.

<First Processing Mode>

First, the aforementioned first processing mode (the zoom processing mode for a super-wide angle endoscope) will be described.

The electronic zoom setting section 34 in the video processor 3 is assumed to receive a zoom processing mode setting instruction from the keyboard 39 or the like, and receive an instruction of setting the first processing mode (the zoom processing mode for a super-wide angle endoscope) as the electronic zoom processing.

At this time, the electronic zoom setting section 34 generates a "zoom processing mode setting instruction signal" for selectively setting the first processing mode, and transmits the zoom processing mode setting instruction signal to the CPU 31.

When the CPU 31 receives the "zoom processing mode setting instruction signal" that selectively sets the first processing mode, and receives the "menu screen generation instruction signal" from the electronic zoom setting section 34, the CPU 31 transmits predetermined "menu screen generation information" to the menu screen generation section 37 to display a menu screen exclusive to a super-wide angle endoscope on the monitor 5.

Thereafter, the menu screen generation section 37 receives the "menu screen generation information", generates a menu screen signal exclusive to a super-wide angle endoscope illustrated in FIG. 11 or FIG. 12, for example, and transmits the menu screen signal exclusive to a super-wide angle endoscope to the combining section 38, under control of the CPU 31.

The combining section 38 switches to the menu screen signal generated in the menu screen generation section 37 in place of the endoscope image signal going through the processing in the electronic zoom processing section 36, and outputs the menu screen signal to the observation monitor 5. At this time, on the observation monitor 5, the menu screen exclusive to a super-wide angle endoscope is displayed as illustrated in FIG. 11 or FIG. 12.

Here, in the video processor 3 of the present embodiment, when the zoom processing mode is set at the zoom processing mode for a super-wide angle endoscope (the first processing mode) as the electronic zoom processing mode by the CPU 31 or the like, either one of the aforementioned two processing patterns, that is, the first processing pattern (the processing pattern in two steps) and the second processing pattern (the processing pattern in three steps) can be selected, concerning zoom processing.

Hereinafter, a selection operation of the processing pattern will be described.

FIG. 11 illustrates a menu screen 60*a* exclusive to a super-wide angle endoscope at a time of the first processing pattern being selected, and FIG. 12 illustrates a menu screen 60*b* exclusive to a super-wide angle endoscope at a time of the second processing pattern being selected.

As illustrated in FIG. 11 and FIG. 12, on the menu screens 60*a* and 60*b* exclusive to a super-wide angle endoscope, a first magnification factor display section 61 that shows a value of a scaling factor B that is a first magnification factor, and a second magnification factor display section 62 showing a value of a scaling factor C that is a second magnification factor are displayed.

Here, FIG. 11 and FIG. 12 illustrate s state at a time of "1.2 times" is set as the first magnification factor (the scaling factor B), and "1.6 times" is set as the second magnification factor (the scaling factor C). Note that in the present embodiment, specific values of the magnification factors are arbitrary values by an operation of the keyboard 39 by a user operation, or can be selected from values prepared in advance.

Further, on each of the menu screens 60*a* and 60*b* exclusive to a super-wide angle endoscope, a display section 63 that displays whether or not to use the scaling factor B which is the first magnification factor is displayed. As illustrated in FIG. 11, on the menu screen 60*a* exclusive to a super-wide angle endoscope corresponding to the first processing pattern (the switching processing in two steps), the display section 63 shows that the scaling factor B which is the first magnification factor is not used, whereas as illustrated in FIG. 12, on the menu screen 60*b* exclusive to a super-wide endoscope corresponding to the second processing pattern (the cyclic switching processing in three steps), the display section 63 shows that the scaling factor B which is the first magnification factor is used.

As described above, when the electronic zoom processing in the video processor 3 is set at the zoom processing mode exclusive to a super-wide angle endoscope (the first processing mode) under control of the CPU 31, the menu screen exclusive to a super-wide angle endoscope is displayed on the observation monitor 5.

Now the first processing pattern (the processing pattern in two steps) is assumed to be selected by the operation of the keyboard 39 (or the electronic zoom setting section 34) in a state where the first processing mode (the zoom processing mode for a super-wide angle endoscope) is set.

At this time, the CPU 31 transmits predetermined menu screen generation information to the menu screen generation section 37 to display the menu screen 60*a* exclusive to a super-wide angle endoscope (refer to FIG. 11) corresponding to the first processing pattern as the menu screen exclusive to a super-wide angle endoscope which is displayed on the observation monitor 5.

Here, it is clearly shown on the processing pattern selection display section 63 in the menu screen 60*a* for super-wide angle endoscope illustrated in FIG. 11 that the scaling factor B which is the first magnification factor is not used, and the user can recognize that the first processing pattern that performs processing in two steps of the non-execution state (including one time) of the electronic zoom processing and the electronic zoom processing with the second magnification factor (1.6 times now) is selected, as the present processing pattern.

In this way, when the endoscope is connected to the video processor 3 in the state where the aforementioned first processing mode (the zoom processing mode for a super-wide angle endoscope) is set by control of the CPU 31, the scope identification section 32 acquires identification information stored in the identification information storage section 24 in the endoscope 2 under control of the CPU 31, identifies the type of the endoscope, and thereafter transmits an identification result to the CPU 31 as scope identification information.

When the CPU 31 determines that the endoscope which is connected is the super-wide angle endoscope 2 based on the scope identification information from the scope identification section 32 thereafter, the CPU 31 executes predetermined zoom control by the zoom processing mode for a super-wide angle endoscope (the first processing mode) which is set by the aforementioned operation.

More specifically, when the first processing pattern is selected as the present processing pattern by the aforementioned operation, for example, the CPU 31 controls the respective circuits to perform the processing in two steps of the non-execution state of the electronic zoom processing (including one time) and the electronic zoom processing with the second magnification factor (1.6 times now).

That is, when the electronic zoom setting section 34 or the scope switch 23 is operated in the state where the first processing pattern is selected, a "zoom operation signal" is inputted to the CPU 31 each time the electronic zoom setting section 34 or the scope switch 23 is operated.

Each time the CPU 31 receives the "zoom operation signal", the CPU 31 drives the cutout position setting section 35 and the electronic zoom processing section 36, and the non-execution state of the electronic zoom processing and the electronic zoom processing with the second magnification factor (1.6 times) are alternately switched.

In the present embodiment, in the state where the first processing mode (the zoom processing mode for a super-wide angle endoscope) is set, the CPU 31 receives the "processing pattern selection instruction signal" from the electronic zoom setting section 34 and can selectively switch the second processing pattern (the processing pattern in three steps) besides the first processing pattern (the processing pattern in two steps) as described above.

More specifically, now in the state where the first processing mode (the zoom processing mode for a super-wide angle endoscope) is set, the second processing pattern (the processing pattern in three steps) is assumed to be selected by the operation of the electronic zoom setting section 34.

At this time, the CPU 31 transmits predetermined menu screen generation information to the menu screen generation section 37 to display the menu screen 60*b* exclusive to a super-wide angle endoscope (refer to FIG. 12) corresponding to the second processing pattern, as the menu screen exclusive to a super-wide angle endoscope which is displayed on the observation monitor 5.

Here, it is clearly shown on the display section 63 in the menu screen 60*b* exclusive to a super-wide angle endoscope illustrated in FIG. 12 that the scaling factor B which is the first magnification factor is used, and the user can recognize that the second processing pattern that performs processing in three steps of the non-execution state (including one time) of the electronic zoom processing, the electronic zoom processing with the first magnification factor (1.2 times now), and the electronic zoom processing with the second magnification factor (1.6 times now) is selected, as the present processing pattern.

Further, when the electronic zoom setting section 34 or the scope switch 23 is operated in the state where the second processing pattern is selected, a "zoom operation signal" is inputted to the CPU 31 each time the electronic zoom setting section 34 or the scope switch 23 is operated as described above.

Each time the CPU 31 receives the "zoom operation signal", the CPU 31 drives the cutout position setting section 35 and the electronic zoom processing section 36, and the non-execution state of the electronic zoom processing, the electronic zoom processing with the first magnification factor (1.2 times) and the electronic zoom processing with the second magnification factor (1.6 times) are cyclically switched.

<Second Processing Mode>

Next, the aforementioned second processing mode (the zoom processing mode for a single visual field endoscope) will be described.

The electronic zoom setting section 34 in the video processor 3 is assumed to receive the zoom processing mode setting instruction from the keyboard 39 or the like, and receive an instruction of setting the second processing mode (the zoom processing mode for a single visual field endoscope) as the electronic zoom processing.

At this time, the electronic zoom setting section 34 generates a "zoom processing mode setting instruction signal" for selectively setting the second processing mode, and transmits the zoom processing mode setting instruction signal to the CPU 31.

The CPU 31 receives the "zoom processing mode setting instruction signal" that is to set the second processing mode selectively, and controls the respective circuits to operate in accordance with the second processing mode.

When an endoscope is connected to the video processor 3, and the CPU 31 determines that the connected endoscope is a single visual field endoscope other than the super-wide angle endoscope 2 based on the scope identification information from the scope identification section 32, in the state where the aforementioned second processing mode (the zoom processing mode for a single endoscope) is set by control of the CPU 31, the CPU 31 controls the respective circuits to execute the electronic zoom processing in the video processor 3 in the zoom processing mode for a single visual field endoscope.

That is, the video processor 3 of the present embodiment is configured to be set to the second processing pattern (the processing pattern in three steps) as for the electronic zoom processing when the electronic zoom processing mode is set at the zoom operation mode for a single visual field (the second processing mode) by the CPU 31.

When the electronic zoom setting section 34 or the scope switch 23 is operated in the state where the second processing pattern is selected, a "zoom operation signal" is inputted to the CPU 31 each time the electronic zoom setting section 34 or the scope switch 23 is operated, and the CPU 31 drives the cutout position setting section 35 and the electronic zoom processing section 36, and can cyclically switch the non-execution state of the electronic zoom processing, the electronic zoom processing with the first magnification factor (1.2 times) and the electronic zoom processing with the second magnification factor (1.6 times).

In this way, when the ordinary endoscope of a single visual field is connected to the video processor 3, the video processor 3 of the present embodiment can effectively use the magnification factor switching processing function in three steps which the video processor 3 originally includes.

As described above, according to the video processor 3 of the first embodiment, the type of the endoscope which is connected to the video processor is identified, and when a super-wide angle endoscope that acquires a so-called forward visual field screen and a sideward visual field screen is connected, the magnification factor switching processing in two steps of switching the non-execution state (including one time) of the electronic zoom processing and the electronic zoom processing with the second magnification factor (1.6 times, for example) is enabled, whereby an ordinary super-wide angle screen (the forward visual field screen+the sideward visual field screen) and a screen of only the forward visual field are made switchable with one touch.

When the endoscope which is connected to the video processor is an ordinary endoscope of a so-called single visual field, the magnification factor switching processing function in three steps which is originally included by the video processor can be effectively used.

In this way, the video processor 3 of the first embodiment can provide an image processing apparatus that can change the number of steps of changing the electronic zoom magnification factor in accordance with the type of the endoscope which is connected.

Second Embodiment

Next, a second embodiment of the present invention will be described.

In a video processor of the second embodiment of the present invention, a basic component is similar to the basic component of the first embodiment, but a method for selecting the first processing pattern and the second processing pattern differs from the selection method of the first embodiment.

Accordingly, only a part different from the first embodiment will be described here, and explanation of similar parts to the parts of the first embodiment will be omitted here.

Figure 13:
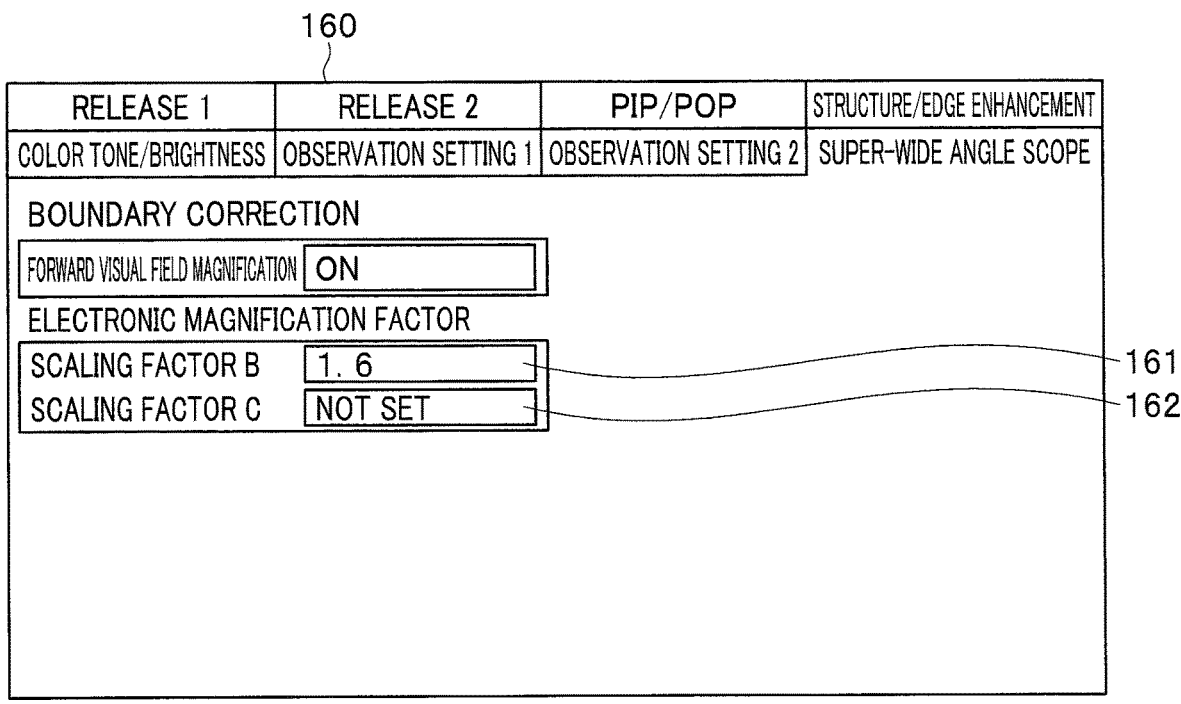
FIG. 13 is a view illustrating an example of a menu screen that is generated in a menu screen generation section in an endoscope system including an image processing apparatus of a second embodiment of the present invention.

FIG. 13 is a view illustrating an example of a menu screen that is generated in the menu screen generation section in an endoscope system including an image processing apparatus of the second embodiment of the present invention.

In the video processor 3 in the second embodiment, when the CPU 31 determines that the endoscope which is connected to the video processor 3 is the super-wide angle endoscope 2, the CPU 31 controls the menu screen generation section 37 and causes the observation monitor 5 to display a menu screen 160 exclusive to a super-wide angle endoscope as illustrated in FIG. 13.

In the second embodiment, as illustrated in FIG. 13, a display section 161 showing a value of the scaling factor B which is the first magnification factor, and a display section 162 that shows a value of the scaling factor C which is the second magnification factor are also displayed on the menu screen 160 exclusive to a super-wide angle endoscope.

Further, in the second embodiment, it is possible to set the zoom scaling factor (1.6 times, for example) at which the visual field ratio of the forward visual field reaches 100%, as the scaling factor B which is the first magnification factor.

When the zoom scaling factor (1.6 times, for example) at which the visual field ratio of the forward visual field described above reaches 100% is set as the scaling factor B which is the first magnification factor by the operation of the electronic zoom setting section 34 or the like in the state where the first processing mode (the zoom processing mode for a super-wide angle endoscope) is set, the CPU 31 determines that the first processing pattern (the processing pattern in two steps) is selected.

Thereafter, when the electronic zoom setting section 34 or the scope switch 23 is operated in the state where the first processing pattern is selected in the video processor 3 of the second embodiment, a "zoom operation signal" is inputted to the CPU 31 each time the electronic zoom setting section 34 or the scope switch 23 is operated, whereby the CPU 31 drives the cutout position setting section 35 and the electronic zoom processing section 36, and the non-execution state of the electronic zoom processing and the electronic zoom processing with the first magnification factor (1.6 times) are alternately switched.

Note that when the zoom magnification factor (1.6 times, for example) at which the visual field ratio of the forward visual field described above reaches 100% is set as the scaling factor B which is the first magnification factor, it is determined that the scaling factor C which is the second magnification factor is not set, and the effect is displayed on the display section 162.

The other operation and effect are similar to the operation and effect of the first embodiment.

As described above, according to the video processor of the second embodiment, the image processing apparatus can be provided, which exhibits a similar effect to the aforementioned first embodiment, and is capable of changing the number of changing steps of the electronic zoom magnification factor in accordance with the type of the endoscope which is connected.

Third Embodiment

Next, a third embodiment of the present invention will be described.

In a video processor of the third embodiment of the present invention, a basic component is similar to the basic component of the first embodiment, and here, only a part different from the part of the first embodiment will be described, and explanation of the parts similar to the parts of the first embodiment will be omitted.

In each of the aforementioned first and second embodiments, the type of the endoscope connected to the video processor 3 is identified, and when it is determined that the super-wide angle endoscope 2 is connected, the processing mode is set at the first processing mode (the zoom processing mode for a super-wide angle endoscope), the menu screen exclusive to a super-wide angle endoscope is displayed, and the aforementioned first processing pattern and second processing pattern are selected by the operation of the electronic zoom setting section 34, whereas a video processor 3 of the third embodiment automatically sets the processing mode at the first processing mode (the zoom processing mode for a super-wide angle endoscope) in accordance with an identification result of a type of an endoscope, and selects the first processing pattern.

Note that in the third embodiment, the processing pattern may be also configured to be changed by a manual operation after the first processing mode is automatically set, and the first processing pattern is selected.

As described above, according to the video processor of the third embodiment, the image processing apparatus can be provided, which can change the number of changing steps of the electronic zoom magnification factor more easily in accordance with the type of an endoscope which is connected.

The present invention is not limited to the aforementioned embodiments, but various changes, alterations and the like are made within the range without changing the gist of the present invention.

What is claimed is:

1. A video processor provided so that an endoscope that picks up an image of a subject is connectable to the video processor, comprising:
   an identification section configured to identify a kind of the endoscope which is connected to the video processor;
   an electronic zoom processing section capable of executing electronic zoom processing of magnifying by a first magnification factor and a second magnification factor larger than the first magnification factor to an image pickup signal of an image picked up by the endoscope;
   a zoom operation signal input section configured to receive a zoom operation signal from a zoom operation section configured to instruct execution of the electronic zoom processing by the electronic zoom processing section; and
   a mode setting section configured to set the video processor to a first mode of enabling selection of a first processing pattern that alternately switches a non-execution state of the electronic zoom processing and electronic zoom processing with the second magnification factor each time the zoom operation signal is inputted, and a second processing pattern that cyclically switches the non-execution state of the electronic zoom processing, electronic zoom processing with the first magnification factor and the electronic zoom processing with the second magnification factor each time the zoom operation signal is inputted, when connection of a super-wide angle endoscope that picks up an optical image of a forward visual field and an optical image of a sideward visual field is identified in the identification section, and set the video processor to a second mode enabling selection of the second processing pattern when connection of a single visual field endoscope is identified in the identification section,
   wherein when the mode setting section performs electronic zoom processing by the second magnification factor in the first mode, the electronic zoom processing section cuts out an image so that only the optical image of the forward visual field is displayed out of the optical image of the forward visual field and the optical image of the sideward visual field and magnifies the image with the second magnification factor.

2. The video processor according to claim 1, further comprising:
   a selection instruction signal generation section configured to generate a selection instruction signal for selecting the first processing pattern or the second processing pattern.

3. The video processor according to claim 1,
   wherein the super-wide angle endoscope is an endoscope comprising a first objective optical system configured to form an optical image of a forward visual field, a second objective optical system configured to form an optical image of a sideward visual field that is a visual field around the forward visual field, and an image pickup section configured to pick up the optical images formed in the first and second objective optical systems.

* * * * *

UNITED STATES PATENT AND TRADEMARK OFFICE
CERTIFICATE OF CORRECTION

PATENT NO. : 10,512,393 B2  
APPLICATION NO. : 16/005819  
DATED : December 24, 2019  
INVENTOR(S) : Tatsuhiko Suzuki Page 1 of 1

It is certified that error appears in the above-identified patent and that said Letters Patent is hereby corrected as shown below:

On the Title Page

(30) Foreign Application Priority Data should read:  
Dec. 17, 2015 (JP)...............20015-246466

Signed and Sealed this  
Fifth Day of May, 2020

Andrei Iancu  
*Director of the United States Patent and Trademark Office*